(12) United States Patent
Grinham et al.

(10) Patent No.: US 11,040,734 B2
(45) Date of Patent: Jun. 22, 2021

(54) MOBILITY APPARATUS FOR RADIOGRAPHIC APPLIANCE

(71) Applicants: Cathy J. Grinham, Assonet, MA (US); Robert P. Grinham, Assonet, MA (US)

(72) Inventors: Cathy J. Grinham, Assonet, MA (US); Robert P. Grinham, Assonet, MA (US)

(\*) Notice: Subject to any disclaimer, the term of this patent is extended or adjusted under 35 U.S.C. 154(b) by 320 days.

(21) Appl. No.: 16/047,110

(22) Filed: Jul. 27, 2018

(65) Prior Publication Data

US 2019/0061796 A1 Feb. 28, 2019

Related U.S. Application Data

(60) Provisional application No. 62/538,023, filed on Jul. 28, 2017.

(51) Int. Cl.
*B62B 3/10* (2006.01)
*B62B 3/02* (2006.01)
(Continued)

(52) U.S. Cl.
CPC .............. *B62B 3/02* (2013.01); *A61B 6/4405* (2013.01); *A61B 6/447* (2013.01); *B62B 3/10* (2013.01);
(Continued)

(58) Field of Classification Search
CPC ......... A61B 6/4405; A61B 6/447; A61B 6/14; A61B 6/4411; B62B 3/10; B62B 3/0625; B62B 3/02; B62B 3/04; B62B 81/002; B62B 81/06; B62B 81/12; B62B 81/14; B62B 81/142; B22C 6/04; B22C 85/0089
See application file for complete search history.

(56) References Cited

U.S. PATENT DOCUMENTS 3,363,787 A \* 1/1968 Macomber ................ B62B 3/04
414/444
3,746,360 A \* 7/1973 Crawford .................. B62B 1/12
280/47.12
(Continued)

FOREIGN PATENT DOCUMENTS

GB 2278318 A \* 11/1994 ............... B62B 1/14

*Primary Examiner* — Steve Clemmons
(74) *Attorney, Agent, or Firm* — Armis IP Law, LLC (57) ABSTRACT

A mobility apparatus for an imaging appliance such as a panoramic radiograph machine allows single-operator transport for on-site usage with ambulatory challenged patients. A counterbalanced pivot interface integrates the imaging appliance with a motorized transport vehicle for disposing the appliance securely on the vehicle, while the counterbalanced pivot interface allows positioning to an operational upright orientation for on-site usage. The imaging appliance includes modifications to a stock appliance for adapting the pivot interface for mobility and for usage with ADA (Americans with Disabilities Act) affected patients, such as wheelchair and scooter bound individuals. The modifications include a truncated base and truncated vertical riser, coupled with a counterbalance mass on the vehicle to maintain stability in the deployed and transportable positions. The lowered vertical riser permits the imaging mechanism to descend to accommodate seated patients.

10 Claims, 12 Drawing Sheets

(51) Int. Cl.
*A61B 6/00* (2006.01)
*A61B 6/14* (2006.01)

(52) U.S. Cl.
CPC ............ *A61B 6/14* (2013.01); *A61B 6/4411* (2013.01); *B62B 2206/04* (2013.01)

(56) References Cited

U.S. PATENT DOCUMENTS

| | | | | |
|---|---|---|---|---|
| 3,939,999 A * | 2/1976 | Nielson | .................... | B62B 1/14 |
| | | | | 414/444 |
| 5,246,239 A * | 9/1993 | Braden | .................... | B62B 1/06 |
| | | | | 280/47.24 |
| 5,318,400 A * | 6/1994 | Nijenhuis | ............. | B62B 5/0089 |
| | | | | 414/441 |
| 5,449,267 A * | 9/1995 | Ablabutyan | .............. | B60P 1/43 |
| | | | | 187/242 |
| 5,547,035 A * | 8/1996 | Berry | .................... | B62D 51/04 |
| | | | | 180/11 |
| 5,683,221 A * | 11/1997 | Ablabutyan | .......... | B60P 1/4457 |
| | | | | 410/94 |
| 5,870,788 A * | 2/1999 | Witkin | .................... | A61G 3/061 |
| | | | | 14/69.5 |
| 6,237,925 B1 * | 5/2001 | Koenig | .................... | B62B 1/12 |
| | | | | 280/47.28 |
| 6,430,769 B1 * | 8/2002 | Allen | .................... | A61G 3/061 |
| | | | | 14/69.5 |
| 6,474,930 B1 * | 11/2002 | Simpson | ................ | A01B 73/00 |
| | | | | 269/17 |
| 6,616,173 B2 * | 9/2003 | Jenkins | .................... | B60S 13/00 |
| | | | | 280/47.131 |
| 8,376,612 B2 * | 2/2013 | Takae | .................... | G03B 42/02 |
| | | | | 378/198 |
| 9,156,485 B1 * | 10/2015 | McLardy | ............. | B62B 5/0086 |
| 9,776,650 B1 * | 10/2017 | Berlinger | ................ | B62B 1/12 |
| 9,782,136 B2 * | 10/2017 | Zhou | .................... | A61B 6/4405 |
| 9,888,891 B2 * | 2/2018 | Suuronen | ............ | A61B 6/4266 |
| 9,969,411 B2 * | 5/2018 | Belotti | .................... | B62B 5/06 |
| 10,674,978 B2 * | 6/2020 | Takemoto | ............. | A61B 6/588 |
| 2006/0048310 A1 * | 3/2006 | Tin | ........................ | B66B 9/0853 |
| | | | | 14/2.4 |
| 2011/0142199 A1 * | 6/2011 | Kantor | ................ | A61B 6/4441 |
| | | | | 378/39 |
| 2012/0146625 A1 * | 6/2012 | Grommer | ............... | F16D 25/10 |
| | | | | 324/207.12 |
| 2015/0203137 A1 * | 7/2015 | Lang | .................... | B62B 3/104 |
| | | | | 414/469 |
| 2016/0236699 A1 * | 8/2016 | Wang | ..................... | B62B 1/12 |
| 2016/0374876 A1 * | 12/2016 | Thornton | ............... | A61G 3/061 |
| | | | | 14/69.5 |
| 2017/0129516 A1 * | 5/2017 | Gervais | ..................... | B62B 1/12 |
| 2018/0346009 A1 * | 12/2018 | Mendoza | ................ | B62B 1/002 |
| 2019/0357862 A1 * | 11/2019 | Bailey | ................ | A61B 6/0457 |

* cited by examiner

MOBILITY APPARATUS FOR RADIOGRAPHIC APPLIANCE

RELATED APPLICATIONS

This patent application claims the benefit under 35 U.S.C. § 119(e) of U.S. Provisional Patent App. No. 62/538,023, filed Jul. 28, 2017, entitled "MOBILITY APPARATUS FOR RADIOGRAPHIC APPLIANCE," incorporated herein by reference in entirety.

BACKGROUND

Health care for elderly and mobility challenged patients is a continually evolving social issue as health care technology progresses and enables greater life expectancies. The emerging technology is continually challenged, however, by cost expectations in providing increasingly expensive technology to longer living patients.

Mobility challenged individuals, such as wheelchair-bound and/or elderly individuals, often require transportation to medical facilities for receiving medical care. Some patients are unable to travel to facilities, or encounter substantial hardships to do so. For some ailments and conditions, adequate care is provided on-site at a residence or care facility, due to readily available medical caretakers, equipment and supplies. Certain equipment, such as imaging devices, are defined by large, heavy appliances that are generally permanently installed in a facility. MRI (Magnetic Resonance Imaging) machines, for example, often occupy an entire room. In can be problematic for non-ambulatory or wheelchair/bed bound patients to gain access to imaging equipment since such appliances are generally deemed non-transportable fixtures.

SUMMARY

A mobility apparatus for an imaging appliance such as a panoramic radiograph machine allows single-operator transport for on-site usage with ambulatory challenged patients. A counterbalanced pivot interface integrates the imaging appliance with a motorized transport vehicle for disposing the appliance securely on the vehicle, while the counterbalanced pivot interface allows positioning to an operational upright orientation for on-site usage. The imaging appliance includes modifications to a stock appliance for adapting the pivot interface for mobility and for usage with ADA (Americans with Disabilities Act) affected patients, such as wheelchair and scooter bound individuals. The modifications include a truncated base and truncated vertical riser, coupled with a counterbalance mass on the vehicle to maintain stability in the deployed and transportable positions. The lowered vertical riser permits the imaging mechanism to descend to accommodate seated patients. The counterbalance mass offsets the truncated base and allows the transport vehicle to support the deployed appliance. The counterbalanced pivot interface permits transition from a deployed to a transportable, or stowed, position by pivoting the substantially vertical stance of the appliance to an angled, stowed orientation. The angled orientation provides stability during transport, yet disposes a center of gravity such that a pivoting return to the deployed (vertical) state may be performed by a single operating technician. The pivot interface braces a lower region of an elongated, vertical body of the appliance, and employs elongated braces and spacers on an inclined support surface on the vehicle for hinged support of the appliance while pivoted to the angled orientation for transport.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is a particular configuration of the disclosed approach employing a panoramic radiograph machine as an imaging appliance and a motorized dolly as the transport vehicle. The imaging appliance represents a substantial expense, and secure handling and transport are therefore required. Further, single operator deployment capability is achieved by maintaining an incline of the transport vehicle around a center of gravity of the stowed imaging appliance. This avoids the need for a dead weight lift of the imaging appliance as it merely needs to be "tilted" to pivot into a secure vertical operating position.

The transport vehicle is a modified wheeled vehicle commonly referred to as a handtruck or dolly, available from conventional sources. In the examples shown, the transport vehicle is motorized using a rechargeable electric motor arrangement. Such handtrucks are configured to center a transport weight above main drive wheels for limiting a dead weight borne by the user. In configurations herein, the imaging appliance has a center of gravity substantially centered over the main drive wheels when in a stowed or retracted position. Visually, this takes the appearance of an angled rest position on the inclined bearing surface of the dolly.

Conventional uses of the transport vehicle include transport of heavy, substantially cubical or rectangular loads. The transport vehicle includes an angled planar protrusion, or plate, at a lower end and designed to extend under a bottom surface of the load to be transported. The plate angles backwards in a rotational manner to effectively tilt the load into an angled, balanced position on the transport vehicle bearing surface. Configurations herein modify the conventional transport vehicle to remove the plate for permitting installation of the interface device.

Figure 1:
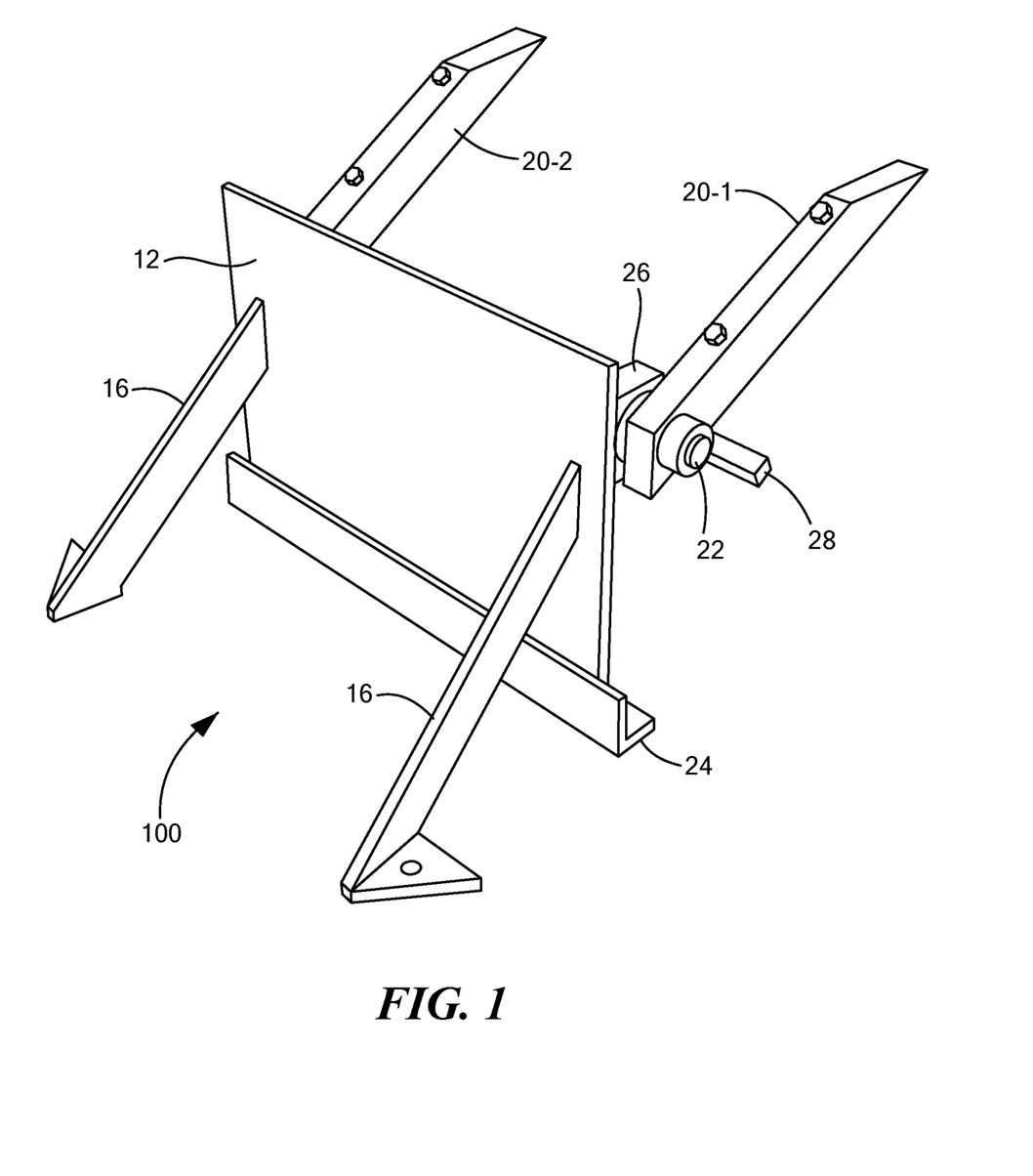
FIG. 1 is a perspective view of an interface device for securing an imaging appliance to a transport vehicle.

FIG. 1 is a perspective view of an interface device securing an imaging appliance to a transport vehicle. Referring to FIG. 1, the interface device 100 is shown after fabrication and before attachment to the transport vehicle and imaging appliance, as will become apparent in the description and Figs. that follow. The device 100 includes an attachment plate 12 welded to a bottom plate 24. The bottom plate 24 extends in parallel communication with a base of the imaging appliance and perpendicular to the attachment plate 12. The bottom plate 24 may be formed from a length of stock angle iron bolted or welded to the inclined load bearing surface of the transport vehicle, discussed further below. Angle braces 16 extend from the attachment plate 12 and terminate substantially coplanar with the bottom plate 24. A shaft 22 extends through pivot blocks 26 secured to the attachment plate 12 and through elongated braces 20-1 . . . 20-2 (20 generally) for pivotal movement between the attachment plate 12 and elongated braces 20. The elongated braces 20 bolt to the transport vehicle, and a lateral spacing member 28 provides an offset from the transport vehicle for proper deployed positioning of the imaging appliance.

Figure 2:
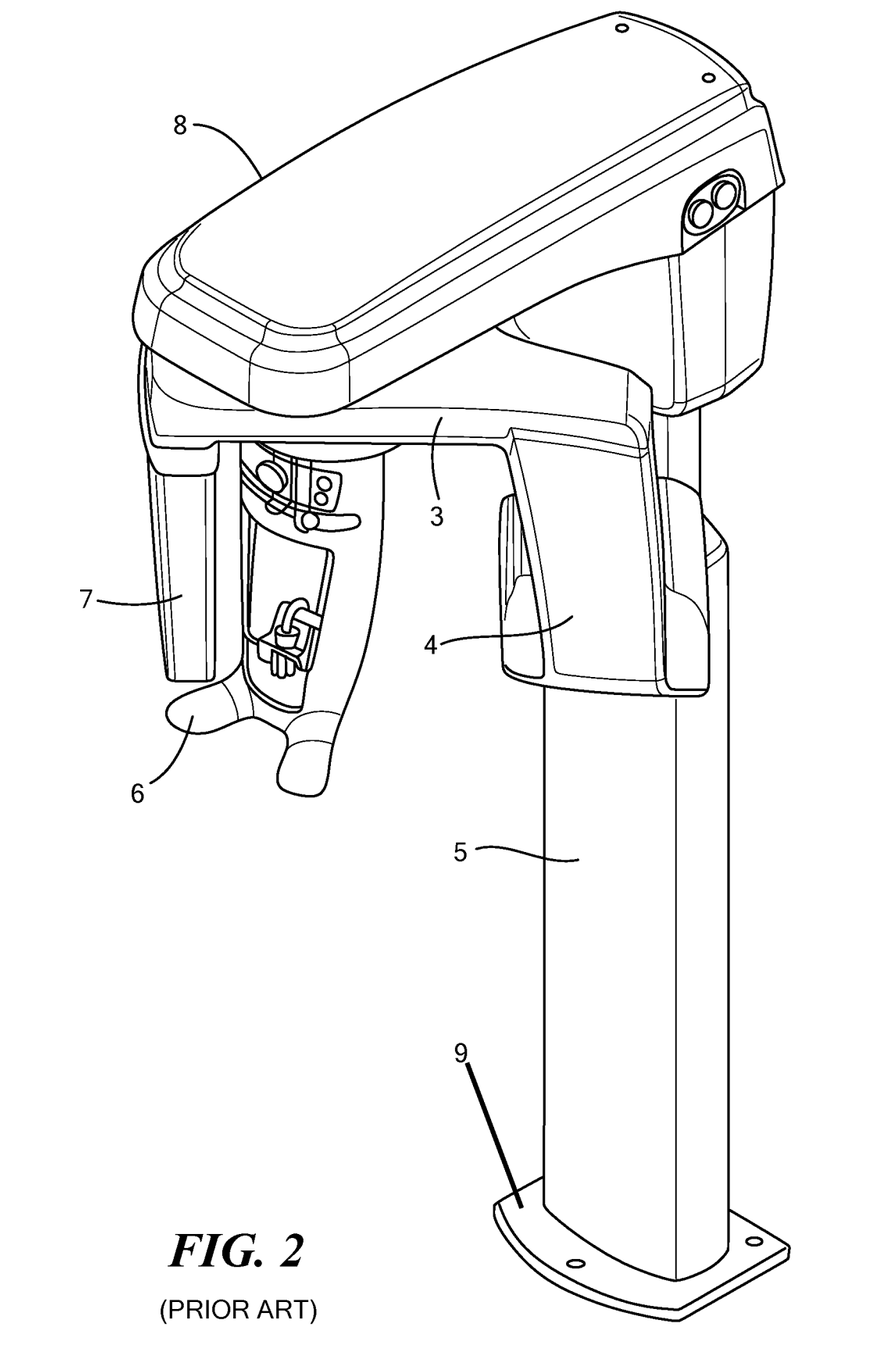
FIG. 2 is a prior art view of an imaging appliance operable for use with the device of FIG. 1.

FIG. 2 is a prior art view of an imaging appliance operable for use with the device of FIG. 1. Referring to FIG. 2, the imaging appliance 50 includes an upright 5 and an overhead support 8. A scan assembly 3 includes an x-ray source 4 and an image sensor 7. A facemask 6 provides positioning for a patient's head between the source 4 and sensor 7 for rotation of the scan assembly 3 around the head of the patient. An imager base 9 includes mounting holes for permanent attachment to a floor, complemented by mounting holes and brackets at the rear for wall attachment, discussed further below. Configurations herein truncate the imager base 9 and reduce the height of the upright 5 for accommodating immobile and wheelchair bound patients by permitting the scan assembly to descend to an appropriate height.

Figure 3:
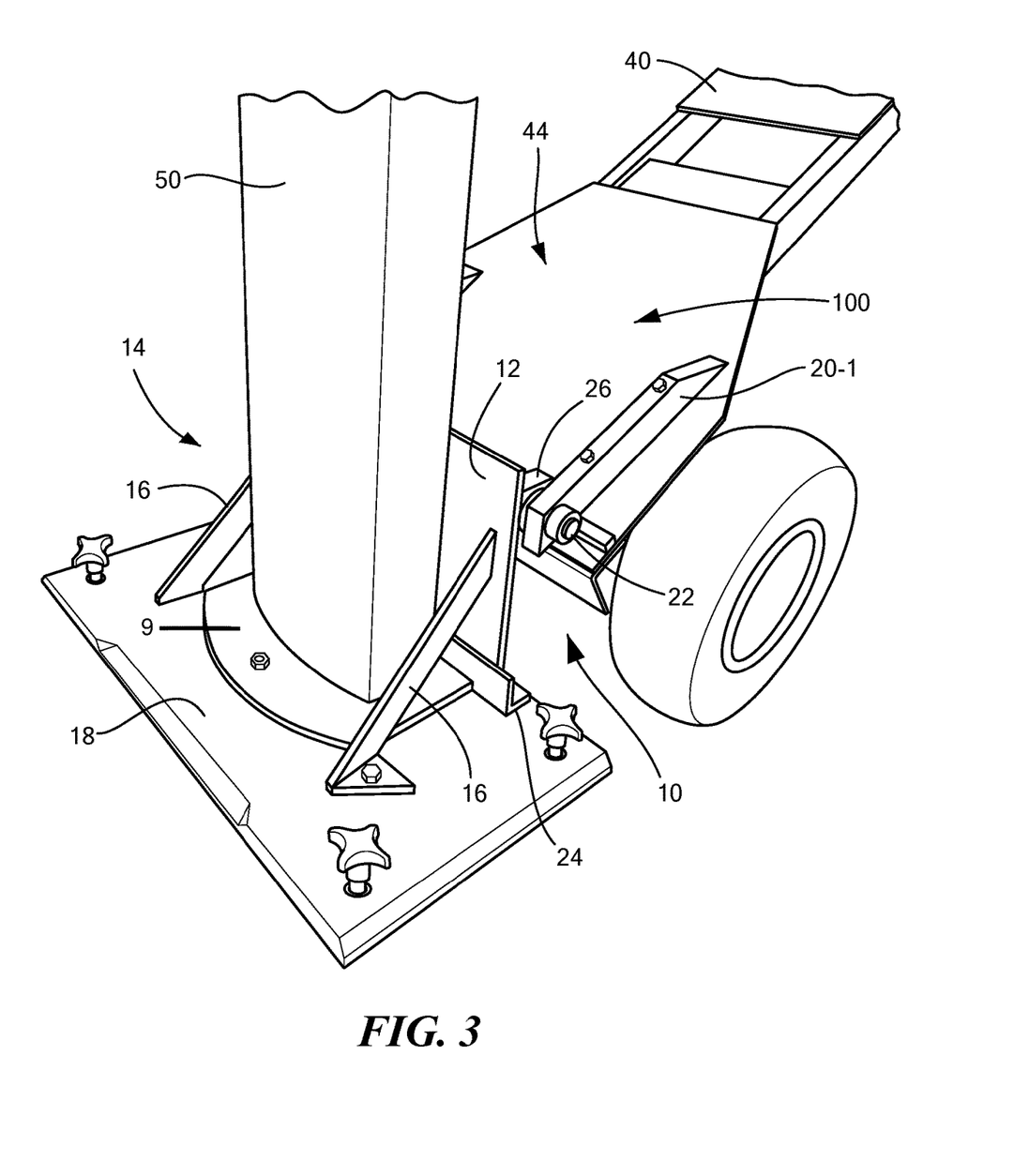
FIG. 3 is a perspective view of the counterbalanced transport interface attaching an imaging appliance to a transport vehicle.
Figure 4:
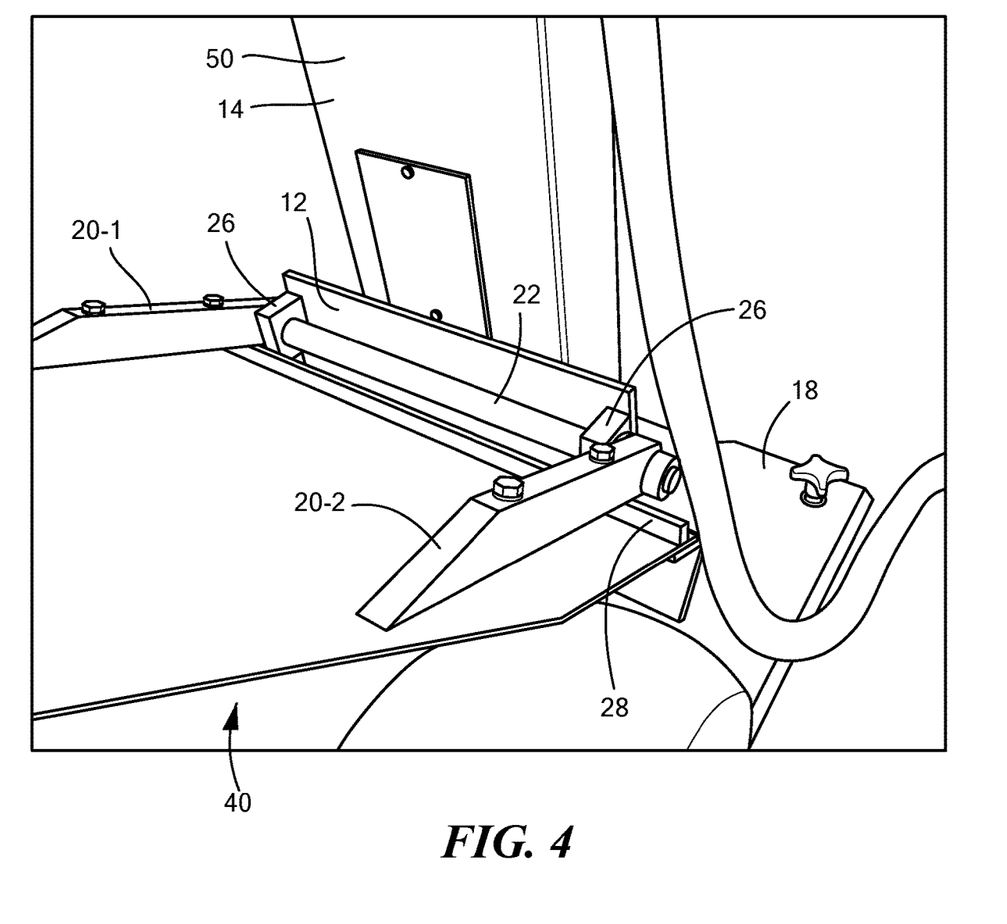
FIG. 4 is an alternate perspective view from the transport vehicle.
Figure 5:
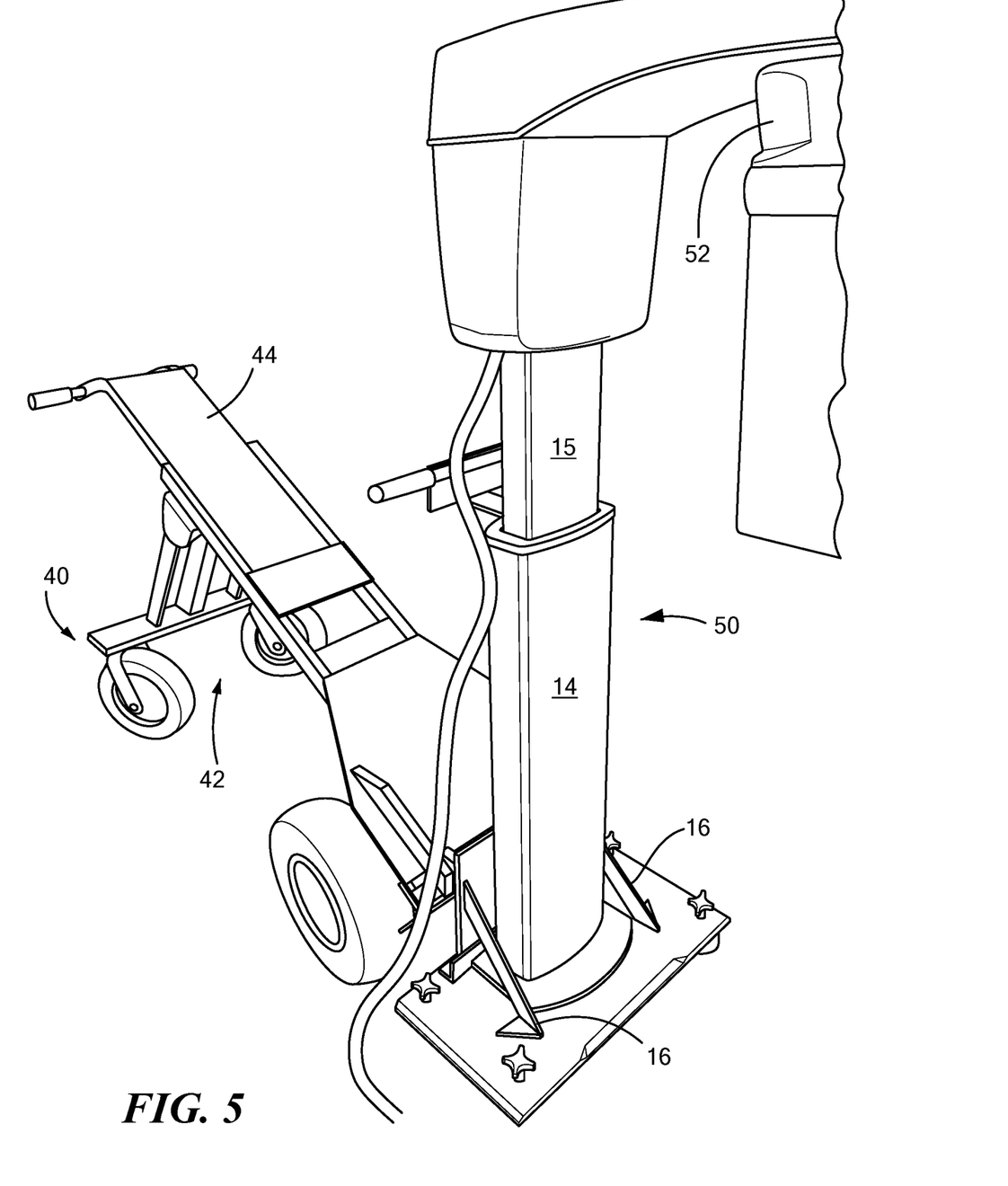
FIG. 5. shows the deployed imaging appliance.

FIG. 3 is a perspective view of the counterbalanced transport interface attaching an imaging appliance to a transport vehicle. Referring to FIG. 3, the counterbalanced transport interface device 100 attaches an imaging appliance 50 to a transport vehicle 40 for transport, deployment and usage thereof. The counterbalanced transport interface device 100 allows pivoting of the imaging appliance 50 to allow transport and on-site deployment at a remote facility while maintaining stability of the appliance through counterbalanced weights and braces. Referring to FIGS. 3-5, the counterbalanced transport interface 100 for the imaging appliance 50 includes the attachment plate 12 secured to a lower region of a lower telescoping portion 14 (upright) supporting a rotating scan assembly 52 of the imaging appliance. A plurality of elongated braces 20-1 . . . 20-2 (20 generally) are adapted for attachment to the transport vehicle 40, such that the elongated braces 20 are configured to bear a weight of the appliance 50 during pivoting between a vertical deployed position and an angled, stowed position. The transport vehicle has an inclined bearing surface defining the stowed position. A pivoting attachment 10 between the attachment plate 12 and the elongated braces 20 is adapted to pivot the imaging appliance 50 to a stowed position, in which the stowed position bears the weight on the pivoting attachment 10 and the transport vehicle 40. The stowed position allows hand guided, rolling transport of the appliance by a single operator via the motorized vehicle 40; alternatively a passive rolling assembly may be employed.

The pivoting attachment 10 is configured to bear the weight as the imaging appliance 50 is deployed by disposing the upright 14 substantially vertical for bearing the weight on a truncated base 18 and the transport vehicle 40. In this deployed position, the transport vehicle 40 is stabilized by a counterbalance mass 42 under the angled transport vehicle surface for limiting angular movement of the upright beyond the deployed, vertical position. The imaging appliance 50 might otherwise exhibit an unstable forward tendency when a rotating scan assembly 52 is extended forward during rotation.

Threaded rubber feet beneath the truncated base 18 position the height of the base such that the hinge stabilizes the upright in a substantially vertical position and the four rubber feet under the base 18 are aligned coplanar with the tires of the transport vehicle 40. A lateral spacing member 28 shims or adjusts the elongated braces 20 to align the hinge with the proper deployed vertical position, discussed further below.

Conventional transport vehicles such as handtrucks are designed to bear weight against an inclined surface for centering a center of gravity of the transported load over the wheels. Such positioning relieves the operator from bearing the load as the wheels tend to balance around the center of gravity. The transport vehicle has an inclined bearing surface defining the stowed position, and the attachment plate is positioned based on a center of gravity of the imaging appliance 50 in the stowed position. The transport vehicle 40 may have and adjustable incline, or may be fixed. An angle of inclination allows the load to be substantially centered over the wheels to bear the dead weight of the load. Generally, the stowed position results from a pivot of not more than 60 degrees. Typically, the stowed position is based on a center of gravity of the imaging appliance and is expected to be a pivot of substantially around 45 degrees. This allows an easier transition to the deployed, or vertical position because the operator does not need to lift the load from horizontal.

A stock transport vehicle often has a perpendicular plate extending from the inclined bearing surface prior to adaptation as described herein. This perpendicular plate is removed to accommodate the interface device.

FIG. 4 is an alternate perspective view from the transport vehicle. Referring to FIGS. 3 and 4, in the example configuration shown, the counterbalanced transport interface 100 further includes a bottom plate 24 extending in parallel communication with the base 18 and perpendicular to the attachment plate 12, and at least one angle brace 16 between the base 18 and the attachment plate 12.

The pivoting attachment 10 further includes a shaft 22 and at least one pivot block 26, such that the shaft 22 extends through the elongated braces 20 and the pivot block 26 for rotational communication therewith, in which the pivot block 26 is secured to the attachment plate 12. The lateral spacing member 28 is disposed between the elongated braces and an inclined bearing surface 44 on the transport vehicle 40, such that the lateral spacing member 28 is in perpendicular orientation with the elongated braces 20 extending across the bottom of the inclined bearing surface 44, and having a stand-off thickness for disposing the pivot block 26 in a noninterfering position with the inclined bearing surface 44 for permitting rotation. Alternatively, the pivot blocks 26 may be mounded on an extension of the elongated braces 20 in a cantilever position extending beyond the inclined bearing surface 44.

FIG. 5. shows the deployed imaging appliance. Referring to FIGS. 3-5, the disclosed approach modifies a stock imaging appliance according to the counterbalanced transport interface device 100. In the therapeutic environment having imaging appliances operable for fixture installation at a treatment facility, the method for adapting an imaging appliance for on-site transport includes attaching the counterbalanced transport interface to the imaging appliance. The method involves reducing a height of a telescoping upright, in which the upright includes a lower portion 14 and an upper portion 15 adapted to dispose within the lower portion 14, thereby reducing a height of the lower portion 14 for permitting greater downward travel of the upper portion 15 as the upper portion supports the rotating scan assembly 52 of the imaging appliance 50. The base 18 of the imaging appliance 50 is truncated for permitting ambulatory assistive vehicles beneath the rotating scan assembly 52, thus allowing a wheelchair or scooter to be wheeled beneath the rotating scan assembly 52.

Figure 6:
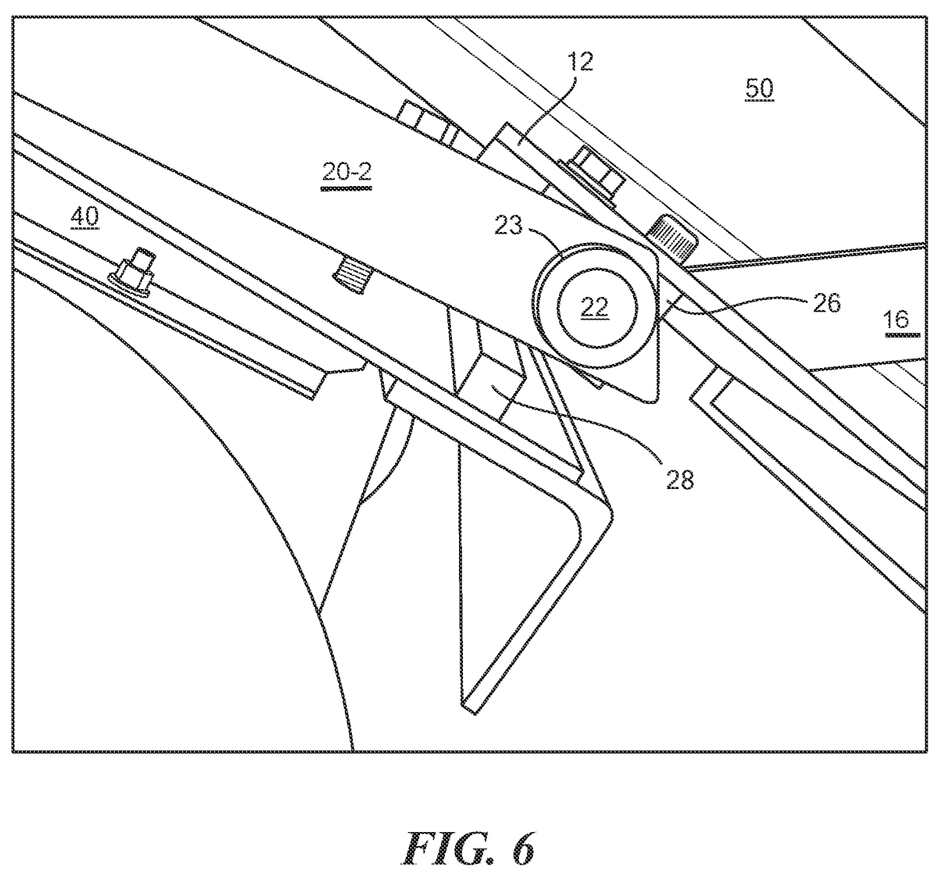
FIG. 6 shows the shaft and pivot mechanism including an offset adjustment on a stowed imaging appliance.

FIG. 6 shows the shaft and pivot mechanism including an offset adjustment on a stowed imaging appliance. The pivoting attachment utilizes the shaft 22 and at least one pivot block 26, such that the shaft extends through the elongated braces 20 and the pivot block 26 for rotational communication. The pivot block 26 is secured to the attachment plate 12 and bears the weight of the imaging appliance 50. Bushings 23 align the shaft 22 between the elongated braces 20, and a plastic washer 25 (FIG. 7) or other friction reducing ring is disposed between. A lateral spacing member 28 provides an offset for permitting rotation of the pivot blocks 26 and to set an appropriate height for the deployed imaging apparatus 50.

Figure 7:
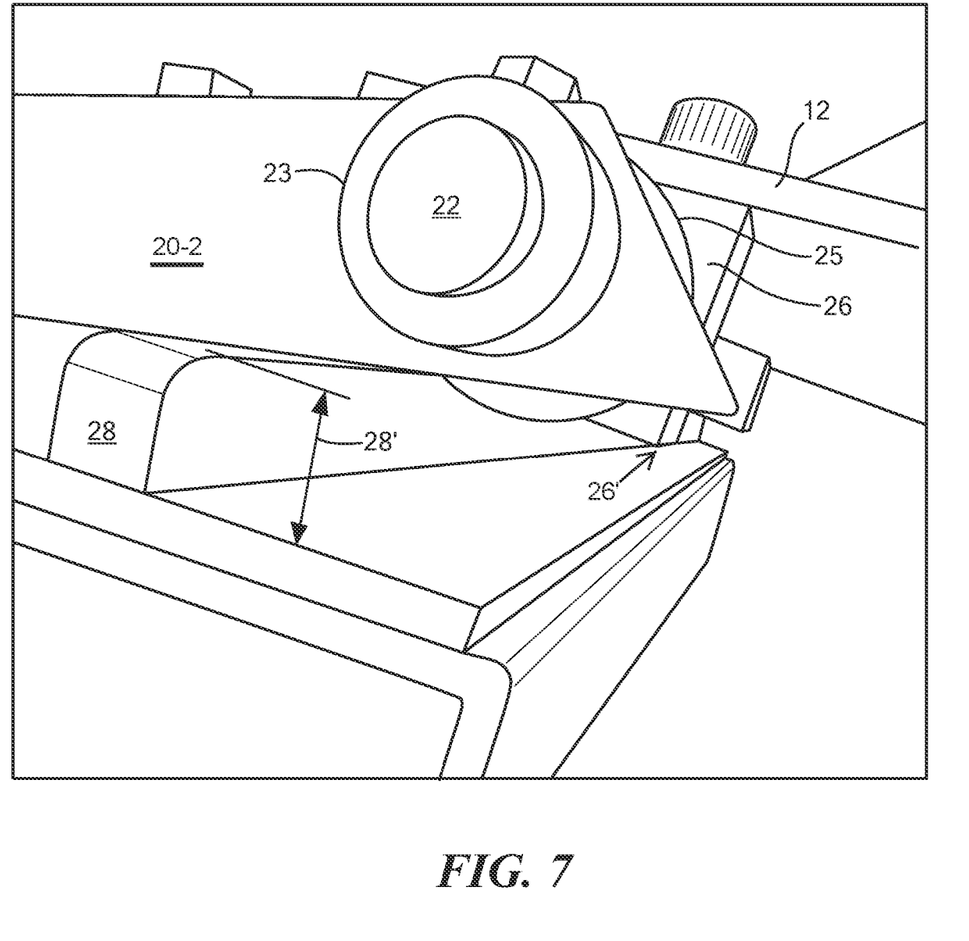
FIG. 7 shows the offset clearances of FIG. 6 in greater detail.

FIG. 7 shows the offset clearances of FIG. 6 in greater detail. Referring to FIGS. 6 and 7, the lateral spacing member 28 between the elongated braces and the transport vehicle, defines an offset thickness based on a distance 28' to an inclined surface bearing the deployed imaging appliance and a rotational clearance of the pivot blocks 26. As the pivot block 26 rotates, a lower edge 26' clears the surface on the transport vehicle based on a sufficient offset distance 28'

Figure 8:
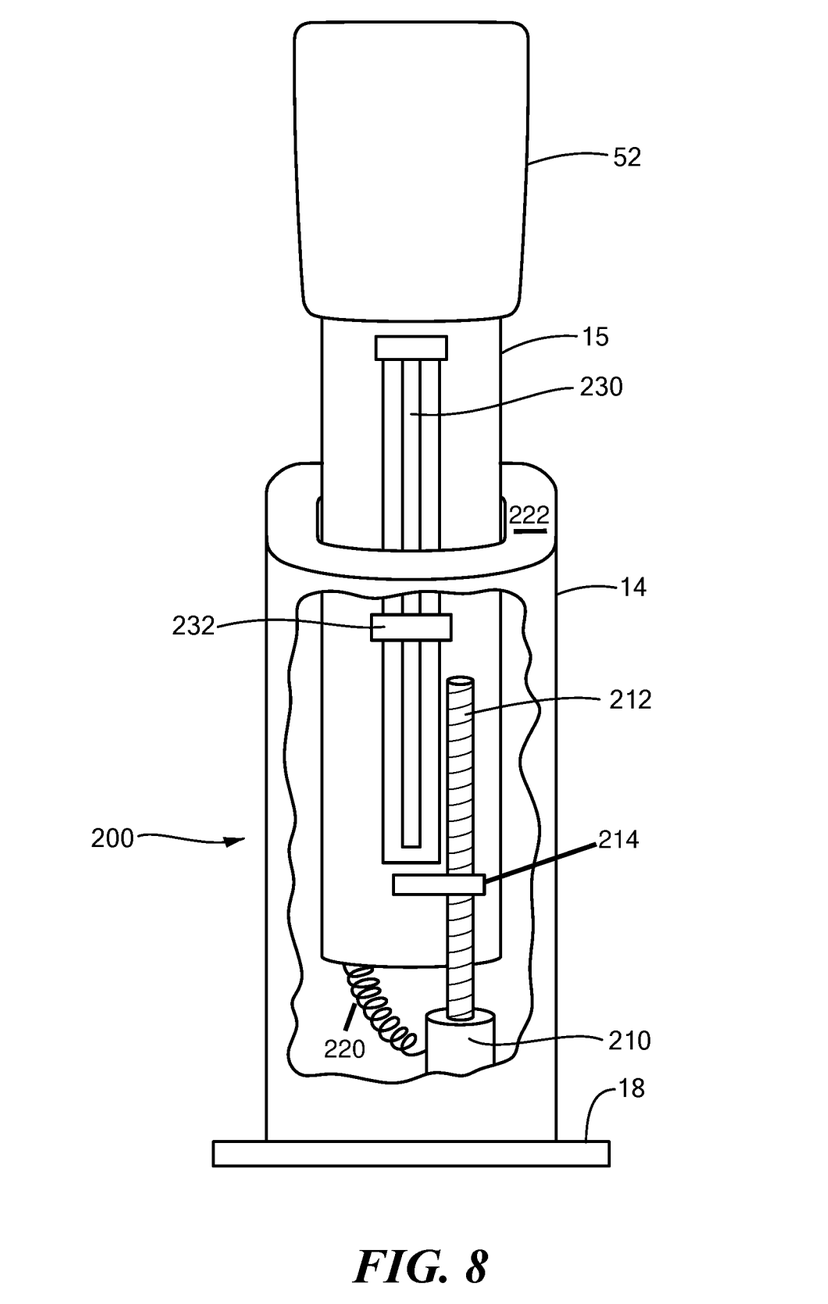
FIG. 8 shows a telescoping upright of the imaging appliance.

FIG. 8 shows a telescoping upright of the imaging appliance. Referring to FIG. 8, the upright 200 employs a telescoping mechanism to permit height adjustment of the rotating scan assembly 52. The telescoping upright includes a lower 14 and upper 15 portion for allowing the scan assembly 52 to dispose around the head of the patient. The disclosed imaging appliance 50 includes a modified telescoping upright for reducing a height of the imaging appliance in the deployed position, such that the reduced height disposes the rotating scan assembly 52 more proximate to the center of gravity and also requires less force to deploy to the vertical position. The reduced height serves the dual purpose of accommodating wheelchair bound patients and facilitating single technician deployment.

The modified telescoping upright 200 includes a truncated lower portion 14 for receiving an upper telescoping portion 15. The upper portion 15 travels up and down inside the lower portion 14 from a screw driven actuator 210. The actuator 210 employs a modified, truncated drive actuator 212 corresponding to the truncated lower portion. In the example configuration, the lower telescoping portion 14 is trimmed by about 8-9 inches, and the actuator 212 a corresponding amount.

As indicated above, conventional approaches employing a stock imaging appliance expect standing patient. Mobility challenged patients may be wheelchair bound and/or unable to stand. Accordingly, the rotating scan assembly 52 must travel downward by receiving the upper portion 15 within the lower portion 14. A drive actuator 210 rotates a threaded adjustment member 212 through a receptacle block 214 attached to the upper portion for disposing the upper portion 15 up and down. A ribbon conductor 220, attached to a side of the upper telescoping portion 15, transmits electrical signals for controlling a telescoping range of movement of the upper telescoping portion 15 into the lower telescoping portion 14. The ribbon conductor 220 is truncated or trimmed to correspond to the top surface 222 of the lower portion 14. In particular arrangements, the truncated ribbon conductor 220 includes a sensing strip 230 for providing position feedback based on varied electrical characteristics from the telescoping movement. The linear sensor 232 is responsive to the position of the sensing strip 232, such as by varied resistance, current or voltage, and determines the travel of the upper portion 15 Recalibration of the head unit 52 height may be performed to ensure correct operation.

Figure 9:
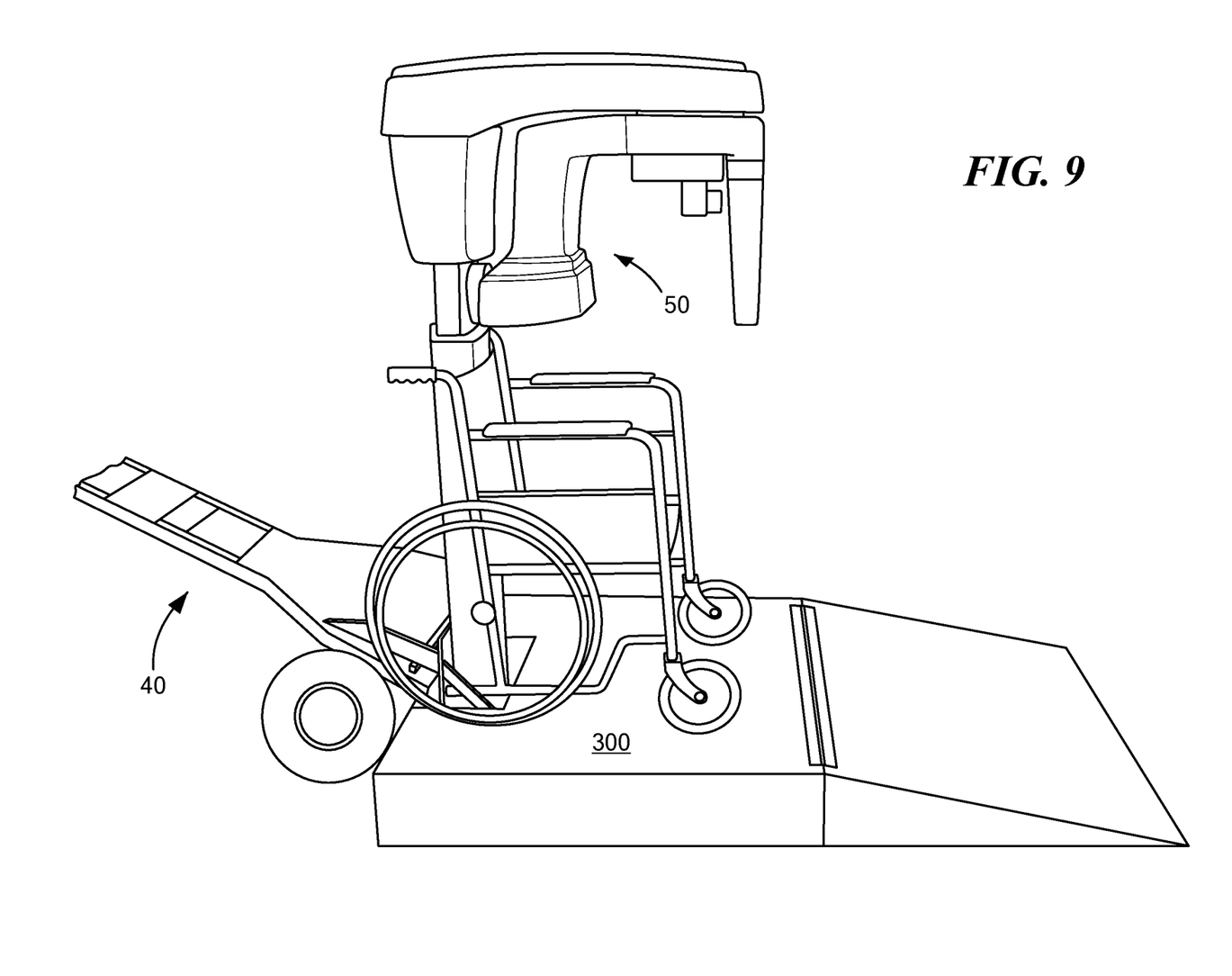
FIG. 9 shows an elevation platform complementing the height clearance afforded by the telescoping upright of FIG. 8.

FIG. 9 shows an elevation platform complementing the height clearance afforded by the telescoping upright of FIG. 8. Referring to FIG. 9, show an elevated inclination for adapting an elevation distance between a rotating scan assembly and a seated patient. An elevated platform, accessible by a removable ramp, has a predetermined height for allowing a wheelchair or other mobility enhancement beneath the rotating scan assembly 52. Various removable ramp assemblies may be provided, with the intent of permitting wheeled access to the elevated platform to allow the scan assembly 52 to be lowered for use with a seated patient. A single piece ramp or multiple ramps may be employed to engage with the elevated platform and provide wheeled access.

Figure 10:
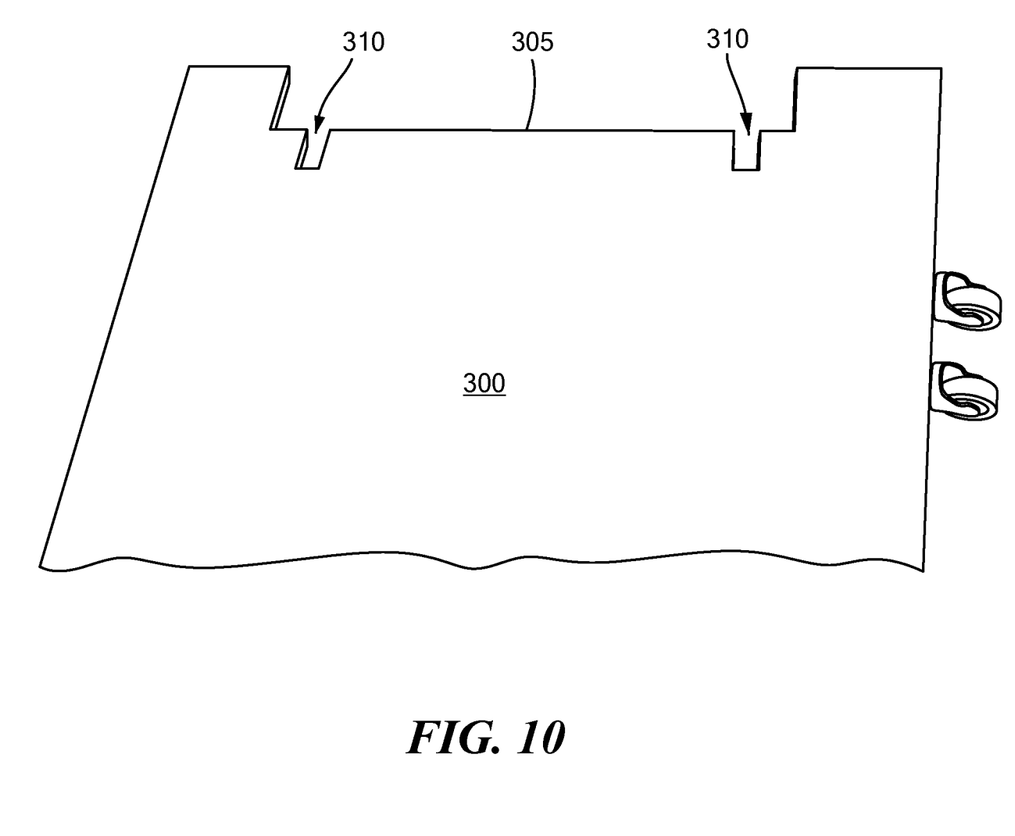
FIG. 10 shows a contour for engaging the elevation platform of FIG. 9 with the deployed imaging appliance.

FIG. 10 shows a contour for engaging the elevation platform of FIG. 9 with the deployed imaging appliance. An elevated platform 300 has a contour 305 corresponding to the deployed imaging appliance. Indentations 310 accommodate the angle braces for flush placement of the platform 300 against the lower telescoping portion 14.

Figure 11:
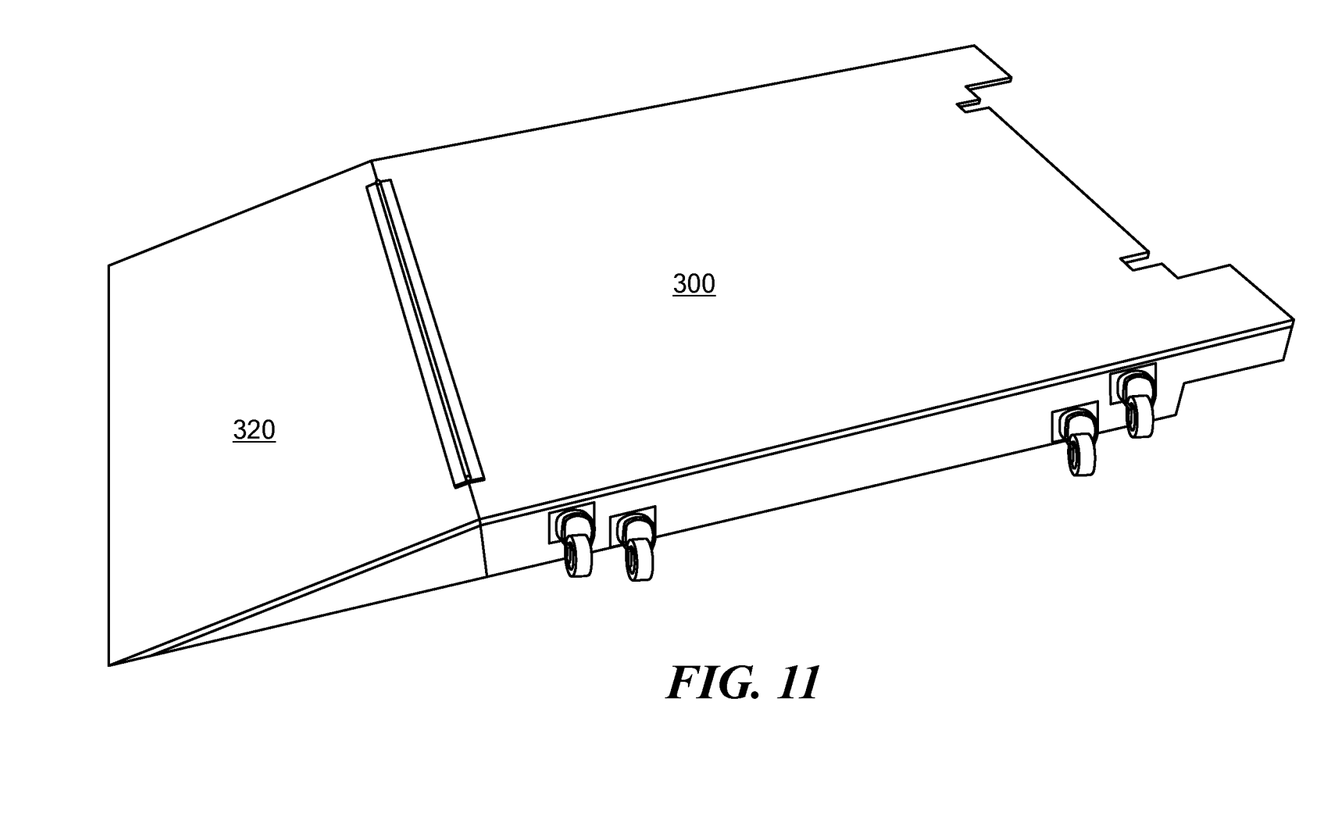
FIG. 11 shows an unfolded view of the elevation platform of FIG. 9.

FIG. 11 shows an unfolded view of the elevation platform 300 of FIGS. 9 and 10. The elevated platform 300 employs a foldable, hinged ramp 320 for facilitating wheelchair access when the platform 300 is deployed beneath the scan assembly.

Figure 12:
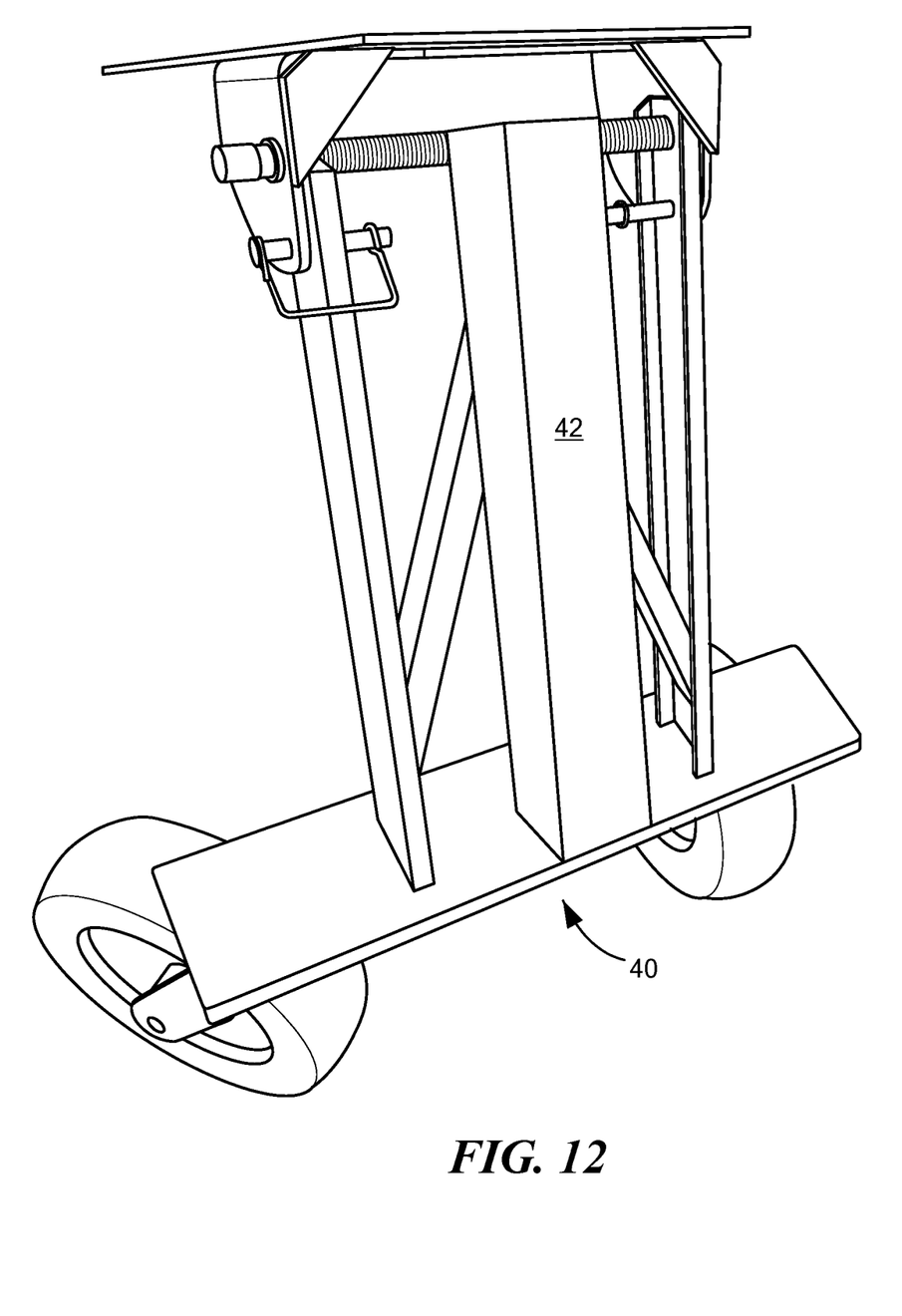
FIG. 12 shows a counterbalance weight for stabilizing the imaging appliance.

FIG. 12 shows a counterbalance weight for stabilizing the imaging appliance. A counterbalance is affixed to a transport vehicle beneath the inclined bearing surface 44, such that a mass of the counterbalance offsets a downward forward rotation of the rotating scan assembly. The imaging appliance is then engaged with the transport vehicle via a counterbalanced transport interface having a pivoting attachment. A welded handle allows the operator to change from the stowed position to standing and operating position.

In a therapeutic environment having imaging appliances operable for fixture installation at a treatment facility, a system configuring an imaging appliance having a rotating scan assembly for on-site transport may provide for on-site usage via an articulated, spring loaded ramp disposed in a box truck and responsive to extend to a ground level for long distance, enclosed movement of the engaged imaging appliance and transport vehicle, While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A pivoting, counterbalanced transport interface device for an imaging appliance, comprising:
   an attachment plate adapted for securement to a lower region of an upright supporting a rotating scan assembly of the imaging appliance;
   a plurality of elongated braces adapted for attachment to a transport vehicle, the elongated braces configured to bear a weight of the imaging appliance during a pivot movement between a vertical deployed position and an angled, stowed position;
   a pivoting attachment between the attachment plate and the elongated braces, the pivoting attachment adapted for rotation of the attachment plate for pivoting the imaging appliance to a stowed position, the stowed position bearing the weight of the imaging appliance on the transport vehicle;
   a bottom plate extending in parallel communication with a truncated base of the imaging appliance and perpendicular to the attachment plate;
   the pivoting attachment further comprising a shaft and at least one pivot block, the shaft extending through the elongated braces and the pivot block for rotational communication therewith, the pivot block secured to the attachment plate;
   the pivoting attachment configured to bear the weight of the imaging appliance as the imaging appliance is deployed by disposing the upright substantially vertical for bearing the weight on the truncated base of the imaging appliance,
   further including a lateral spacing member between the elongated braces and the transport vehicle, the lateral spacing member defining an offset thickness based on a distance to an inclined bearing surface on the transport vehicle and a rotational clearance of the pivot blocks with the inclined bearing surface.

2. The interface device of claim 1 wherein the inclined bearing surface defines the stowed position, and the lateral spacing member disposes the pivot block such that an axis of rotation of the shaft aligns the upright and truncated base on a horizontal surface bearing the imaging appliance in the deployed position.

3. The interface device of claim 1 wherein the inclined bearing surface defines the stowed position, the attachment plate positioned based on a stability of the imaging appliance in the stowed position, the stowed position resulting from a pivot of not more than 60 degrees.

4. The interface device of claim 3 wherein the stowed position based on a center of gravity of the imaging appliance is based on a pivot of substantially around 45 degrees.

5. The interface device of claim 3 wherein the interface device is adapted to engage the imaging appliance via attachment to a modified telescoping upright for reducing a height of the imaging appliance when in the deployed position, the reduced height disposing a rotating scan assembly more proximate to the base for reducing a working range of the imaging appliance and increasing stability between the stowed and deployed positions.

6. The interface device of claim 5 wherein the modified telescoping upright includes:
   a truncated lower portion for receiving an upper telescoping portion therewithin;
   a truncated drive actuator corresponding to the truncated lower portion; and
   a truncated ribbon conductor for transmitting electrical signals for controlling a telescoping range of movement of the upper telescoping portion relative to the lower telescoping portion.

7. The interface device of claim 6 wherein the truncated ribbon conductor includes a sensing strip for providing position feedback based on varied electrical characteristics from the telescoping movement.

8. The interface device of claim 1 wherein the transport vehicle is stabilized by a counterbalance mass for limiting angular movement of the upright beyond the deployed, vertical position.

9. The device of claim 1, wherein the attachment plate aligns with the upright, the attachment plate parallel to the inclined bearing surface in the stowed position and vertical in a deployed position for bearing a weight of the imaging appliance on the base; the attachment plate pivoting in a fixed engagement with the imaging appliance between the stowed and deployed positions.

10. In a therapeutic environment having imaging appliances operable for fixture installation at a treatment facility, a method for adapting an imaging appliance for on-site transport, comprising:
   attaching a transport interface to the imaging appliance, the transport interface including:
      at least one elongated brace adapted for attachment to a transport vehicle;
      an attachment plate adapted for securement to a lower region of an upright supporting a rotating scan assembly of the imaging appliance; and
      a pivoting attachment between the attachment plate and the at least one elongated brace, the pivoting attachment including:
         a shaft and at least one pivot block, the shaft extending through the at least one elongated brace and the pivot block for rotational communication therewith, the pivot block secured to the attachment plate;
         the pivoting attachment adapted for pivoting the imaging appliance to a stowed position, the stowed position bearing the weight of the imaging appliance on the at least one elongated brace,
   the attaching further comprising:
   reducing a height of a telescoping upright, the upright including a lower portion and an upper portion adapted to dispose within the lower portion, reduction including reducing a height of the lower portion by trimming the lower portion for defining a truncated top surface for permitting greater downward travel of the upper portion, the upper portion supporting the rotating scan assembly of the imaging appliance;
   truncating a base of the imaging appliance for permitting ambulatory assistive vehicles beneath the rotating scan assembly;
   affixing a counterbalance to the transport vehicle adapted for transporting the imaging appliance, the counterbalance offsetting a downward forward rotation of the rotating scan assembly;
   inserting a lateral spacing member between the at least one elongated brace and the transport vehicle, the lateral spacing member defining an offset thickness based on a distance to a horizontal surface bearing the imaging appliance and a rotational clearance of the pivot blocks; and engaging the imaging appliance with the transport vehicle via the transport interface having the pivoting attachment.

\* \* \* \* \*